US010621812B1

(12) United States Patent
McNenny (10) Patent No.: US 10,621,812 B1
(45) Date of Patent: Apr. 14, 2020

(54) AUTOMATED TEMPORARY TATTOO AND BODY PAINT KIOSK (71) Applicant: Patrick McNenny, Redwood City, CA (US)

(72) Inventor: Patrick McNenny, Redwood City, CA (US)

( * ) Notice: Subject to any disclaimer, the term of this patent is extended or adjusted under 35 U.S.C. 154(b) by 253 days.

(21) Appl. No.: 15/628,239

(22) Filed: Jun. 20, 2017

Related U.S. Application Data (60) Provisional application No. 62/352,404, filed on Jun. 20, 2016.

(51) Int. Cl.
G07F 17/26 (2006.01)
A61M 37/00 (2006.01)
A61K 8/02 (2006.01)
A61Q 1/02 (2006.01)
A61B 90/00 (2016.01)
B41M 5/382 (2006.01)

(52) U.S. Cl.
CPC .......... *G07F 17/266* (2013.01); *A61K 8/0245* (2013.01); *A61M 37/0084* (2013.01); *A61Q 1/025* (2013.01); *A61B 90/361* (2016.02); *B41M 5/38228* (2013.01)

(58) Field of Classification Search
CPC ................ G07F 17/266; A61K 8/0245; A61M 37/0084; A61Q 1/025; B41M 5/38228; A61B 90/361
See application file for complete search history.

(56) References Cited

U.S. PATENT DOCUMENTS

| 6,295,737 | B2 * | 10/2001 | Patton | ........................ | B41J 2/01 |
| | | | | | 101/35 |
| 6,341,831 | B1 | 1/2002 | Weber et al. | | |
| 8,083,422 | B1 | 12/2011 | Simmons et al. | | |
| 8,634,951 | B2 | 1/2014 | Freeman | | |
| 2002/0070988 | A1 | 6/2002 | Desormeaux | | |
| 2007/0092634 | A1 | 4/2007 | Xingzhu | | |
| 2008/0247637 | A1 | 10/2008 | Gildenberg | | |
| 2011/0298861 | A1 | 12/2011 | Silverbrook | | |
| 2013/0046324 | A1 | 2/2013 | Williams | | |
| 2013/0289671 | A1 | 10/2013 | Homer | | |

FOREIGN PATENT DOCUMENTS

| CN | 1209248 C | 7/2005 |
| CN | 104127955 B | 7/2016 |
| WO | 2015193513 A1 | 12/2015 |

* cited by examiner

Primary Examiner — Henok D Legesse
(74) Attorney, Agent, or Firm — Cramer Patent & Design, PLLC; Aaron R. Cramer (57) ABSTRACT Tattoo and body painting kiosks that print temporary tattoo art onto various body parts of a person. Those kiosks use digital print data of the tattoo to be printed and which can be stored locally, uploaded, or downloaded. The tattoo printing process can utilize a printer that moves in three dimensions to print on a user's body part. Some printers may move three hundred sixty degrees (360°) while others may be fixed. Various printing technologies can be used. In a seated embodiment, a user sits and inserts their body part into an aperture to be printed by a print head. In a standing embodiment, a user locates their body part adjacent a printer to be printed by a print head. In another embodiment, a mechanical arm having a printing device is manually positioned to access a user's body parts.

2 Claims, 10 Drawing Sheets

AUTOMATED TEMPORARY TATTOO AND BODY PAINT KIOSK

RELATED APPLICATIONS

The present invention was first described in and claims the benefit of U.S. Provisional Application No. 62/352,404, filed Jun. 20, 2016, the entire disclosures of which are incorporated herein by reference.

FIELD OF THE INVENTION

The present invention pertains to personal service kiosks. More particularly the present invention relates to a temporary tattoo and body paint kiosk.

BACKGROUND OF THE INVENTION

A tattoo is a body markings made by inks or pigments. Tattoos are widely used to provide individual and group expressions such as belonging or personal statements. While tattoos are very popular in many cultures around the world they have one serious drawback, they are permanent. Not only may a person's personal expression or group identification change over time but tattoos fade, thus reducing their artistic nature. What may have seemed like a great idea at a young age may not seem like such at an advanced age.

One (1) solution to the permanency problems of tattoos are temporary tattoos. Temporary tattoos are not permanent and the tattoo body image can fade away and disappears over time, either from normal skin exfoliation or simply by body washing. Temporary tattoos are highly beneficial to those that want to implement a body expression but do not want that expression to be permanent. For example, temporary tattoo use can be used for short term celebrations such as supporting a local sports team, tourism. Children as well as adults can appreciate that temporary tattoos provide highly flexible body art that can be changed as often as desired or as times change.

One (1) major drawback of temporary tattoos is where to get them. Some temporary tattoos are simply water based images that are readily removed by washing. However, longer lasting temporary tattoos, or more customized temporary tattoos are difficult to get. Often a skilled artisan is required to provide a suitable temporary tattoo.

Therefore, a device for printing a temporary tattoo art image onto a user's body would be beneficial. Even more beneficially would be a temporary tattoo kiosk that prints temporary tattoo art images on a user. More particularly, such a temporary tattoo kiosk should not require a skilled artisan to produce a temporary tattoo art image. Beneficially, such a temporary tattoo kiosk could be implemented as either a self-service facility or one (1) managed by an attendant. Even more beneficially such a temporary tattoo kiosk could receive tattoo art images digitally using either pre-loaded image data, downloaded image data such as over the internet, or uploaded image data such as from a USB or other memory device. Ideally such a device could use ink jet, laser, thermal, air brush, or other spray on printing techniques.

SUMMARY OF THE INVENTION

The principles of the present invention provide for temporary tattoo printing kiosks that produces temporary tattoo art images. Such kiosks may be self-service or they may be operated by an attendant. A temporary tattoo printing kiosk in accord with the present invention receives temporary tattoo art images digitally using pre-loaded image data, downloaded image data, or uploaded image data. The inventive temporary tattoo printing kiosk can use ink jet, laser, thermal, air brush, or other spray on or printing techniques.

A seated tattoo kiosk that is in accord with the present invention includes a vertically elongated cabinet having an aperture that passes into the cabinet, a printing device for printing a tattoo on a body part that passes through the aperture, a seat for a user to sit on to pass a body part through the aperture; and a PRINT switch for causing the printing device to print the tattoo.

The seated tattoo kiosk may produce a temporary tattoo and there may be a video display on the cabinet. That video display is useful for producing an image of the tattoo art that is to be printed. That video display may also produce operating instructions. Preferably the tattoo is derived from digital data. Even more preferably the seated tattoo kiosk may include a data port for inputting a digital version of the tattoo. The seated tattoo kiosk may further comprise a viewing window for enabling viewing of the printing device. In one (1) embodiment, the printing device can print over a three hundred sixty degree (360°) print area.

A standing tattoo kiosk that is in accord with the present invention includes a cabinet, a post adjacent the cabinet, a printer housing having a recessed area, a printing device within the printer housing for printing a tattoo on a body part that is located adjacent the recessed area; and a PRINT switch operatively connected to the printing device for causing the printing device to print the tattoo.

The printer housing may have a recessed area for receiving the body part. Preferably the printer housing is vertically adjustable and includes a locking mechanism for locking the printer housing in position on the pole. In addition, there may be an arm restraint operatively connected to the post for restraining a body part. That tattoo may be a temporary tattoo and there may be a video display on the cabinet. If so that video display may produce an image of the tattoo art to be printed. In practice the tattoo is ideally derived from digital data.

A positionable printing arm tattoo kiosk that is in accord with the present invention includes a vertically elongated cabinet, a printing device for printing a tattoo on a body part; and a positionable mechanical arm having an arm cylinder holding the printing device. That mechanical arm is attached to the cabinet and may be positioned as needed via manual manipulation. In practice that mechanical arm supports three-dimensional positioning via an assembly of linear arm elements interconnected by orbitally manipulated friction-type arm joints.

BRIEF DESCRIPTION OF THE DRAWINGS

The advantages and features of the present invention will become better understood with reference to the following more detailed description and claims taken in conjunction with the accompanying drawing, in which like elements are identified with like symbols, and in which:

DESCRIPTIVE KEY 10 seated temporary tattoo kiosk
20 cabinet
22 front panel
24 left side
26 back panel
28 right side panel
30 arm aperture
31a arm cylinder
31b arm cylinder
31c arm cylinder
34 video display
36 print area
38 viewing window
40 memory device slot
42 PRINT button
60 printing device
61 print aperture
62a printing head
62b printing head
62c printing head
64 Y-axis motor
66 X-axis motor
67 Y-axis guide rail
68a first X-axis guide rail
68b second X-axis guide rail
69a first bearing
69b second bearing
69c third bearing
70a rail mounting bracket
70b rail mounting bracket
72 ribbon cable
80 printing device
82 head positioning member
84 sensor
86 printing gap
88a first X-axis guide rail
88b second X-axis guide rail
89 X-axis guide rail bracket
90 Y-axis guide rail
92 first shaft drive
94 second shaft drive
100 customer/person
101 temporary tattoo art
102 body part
105 arm
110 forearm
115 upper arm
120 shoulder
125 seat
200 standing temporary tattoo kiosk
202 upper cabinet section
204 lower cabinet section
206 cabinet base
210 printer housing
212 recessed area
214 printer positioning sleeve
216 printer positioning sleeve knob
220 post
222 post mounting bracket
230 arm restraint assembly
231 support rod
232 arm saddle
234 arm restraint positioning sleeve
236 arm restraint positioning sleeve knob
300 printing device
302 flexible guide rail
400 positional printing arm tattoo kiosk
402 cabinet
410 mechanical arm
415 arm element
420 arm joint
430 remote arm aperture
435 remote arm cylinder
500 arm restraint assembly
504 elbow restraint
506 wrist restraint
508 base
600 operational block diagram
602-610 operational steps

DETAILED DESCRIPTION OF THE PREFERRED EMBODIMENT

Embodiments of the present invention are depicted in FIGS. 1 through 6. However, the invention is not limited to those specifically described and illustrated embodiments. A person skilled in the art will appreciate that many other embodiments of the invention are possible without deviating from the basic concept of the invention. Any such work around also falls under the scope of this invention. While only three (3) particular embodiments will be illustrated and described, that is for purposes of clarity and disclosure and not by way of limitation of scope.

In the figures like numbers refer to like elements throughout. Additionally, the terms "a" and "an" as used herein do not denote a limitation of quantity, but rather denote the presence of at least one (1) of the referenced items. All directional signals such as front, left, right, back, up and down are taken relative to the orientation shown in the figures.

Figure 1:
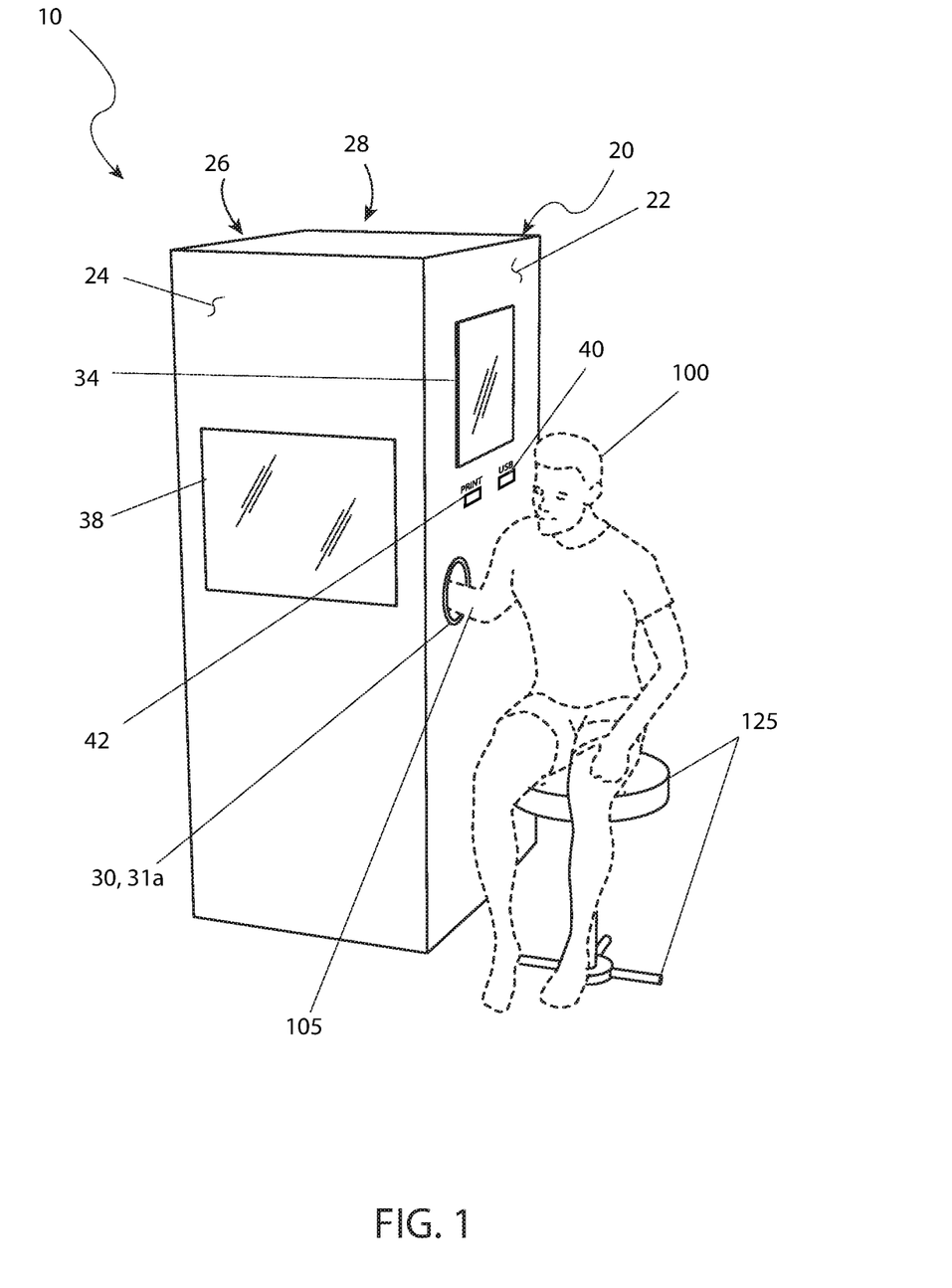
FIG. 1 is a front perspective view of a seated temporary tattoo kiosk 10 that is in accord with the present invention.

Turn now to FIG. 1 for a front perspective view of a seated temporary tattoo kiosk 10 that is in accord with the present invention. The seated temporary tattoo kiosk 10 is a temporary tattoo and body painting service center that prints temporary tattoo art 101 (see FIG. 2a) onto various body parts 102 (such as an arm 105, forearm 110, or upper arm 115) of a user 100. The seated temporary tattoo kiosk 10 maybe a self-service center or it may be managed by one (1) or more attendants. Other temporary tattoo kiosks (described subsequently) can produce temporary tattoo art 101 on other body parts 102.

The seated temporary tattoo kiosk 10, as well as the other kiosks described subsequently, hold or can receive printing data (e.g. a digital image) that is suitable for printing temporary tattoo art 101 upon a body part 102 of the user 100. That printing data may be stored in local memory, it may be uploaded remotely, including wirelessly, or it may be downloaded. The tattoo printing process may utilize ink jet, laser, thermal, air brush, or another printing technique. Temporary tattoo art 101 is herein defined as any artwork printed on a user's body that is not permanent. Temporary tattoo art 101 can be removed such as by washing with water or some other liquid or it may disappear over time from normal skin exfoliation. Temporary tattoo art 101 may be black and white or color or a combination of black and white and color.

The seated temporary tattoo kiosk 10 includes a vertically elongated rectangular cabinet 20 having four (4) sides, including a front panel 22, a left side panel 24, a back panel 26, and a right side panel 28 (the panels 26 and 28 are not directly shown in FIG. 1 because of the perspective angle). Passing through the front panel 22 is an arm aperture 30 that allows the insertion of at least the forearm 110 of a user 100. A viewing window 38 is located on the left side panel 24 to allow observance of the overall process and the output of a printing device 60 (see for example FIG. 2a, but other suitable printing devices are described subsequently) as it applies temporary tattoo art 101 to a user 100. The printing device 60 may be an ink jet printer, a laser printer, a thermal-based printer, an automated air brush, or another printing technique. The seated temporary tattoo kiosk 10 also includes a video display 34 located on the upper portion of the front panel 22 which allows a seated user 100 to, among other things, select the temporary tattoo art 101 to be printed, make various operational adjustments, show the temporary tattoo art 101 as it is being printed, and the like. The seated temporary tattoo kiosk 10 further includes a memory device slot 40 for inputting (downloading) temporary tattoo art 101 data and a "PRINT" button 42 that initiates printing, both of which are located on the front panel 22, and a seat 125.

In use the user 100 sits on the seat 125 during printing. The user 100 would use the video display 34 to select the temporary tattoo art 101 image that they wish to have printed onto their body part 102, possibly from a library of images that are stored in the seated temporary tattoo kiosk 10. Alternatively a user 100 might upload an image of a temporary tattoo art 101 from an internet connection or download an image using a Bluetooth® device or from a personal memory storage device such as, but not limited to: an SD card, a USB flash drive, or some other form of memory media via the memory device slot 40.

Once the desired temporary tattoo art 101 is selected the user 100 inserts at least part of their arm 105 into the seated temporary tattoo kiosk 10 thru an arm aperture 30. Interior lighting could then illuminate a print area 36 (see FIG. 2b) where the temporary tattoo art 101 is to be imaged. Once the arm 105 is in place the user 100 would press the PRINT button 42 to initiate the printing of the selected temporary tattoo art 101 image onto the selected print area 36 of the arm 105.

As noted the seated temporary tattoo kiosk 10 prints a temporary tattoo art 101 image that is derived from digital data. It should also be noted that digital data can be in any of the various imaging formats that are currently available or which may become available. A temporary tattoo art 101 image may be applied for celebrations, advertisement, tourism, or to support one's school or favorite sports team. The seated temporary tattoo kiosk 10 (as well as the other embodiments described herein) will find use in traditional tattoo parlors, shopping centers, hotels, dance clubs, other clubs, and generally just about anywhere.

Figure 2A:
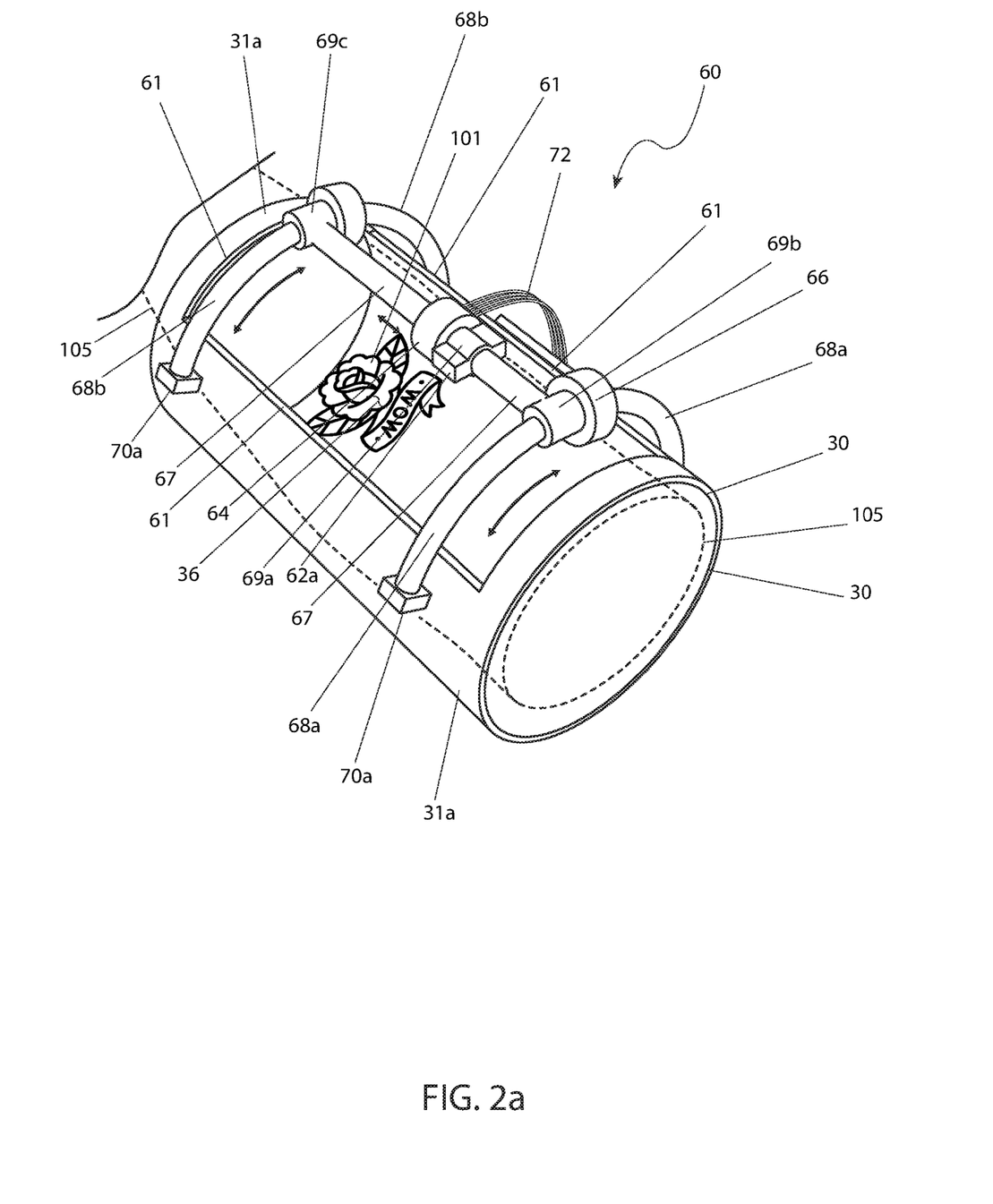
FIG. 2a is a perspective view of a printing device 60 that is suitable for use in the seated temporary tattoo kiosk 10 of FIG. 1.

Refer now to FIG. 2a for a perspective view of a printing device 60 that is suitable for use in the seated temporary tattoo kiosk 10, as well as in other temporary tattoo kiosks that are described subsequently. The printing device 60 has a printing head 62a that is movably (including rotationally) attached to an arm cylinder 31a (also see FIG. 1). The printing head 62a prints temporary tattoo art 101 upon a curved print area 36 of an arm 105 or the like. While the seated temporary tattoo kiosk 10 is illustrated in FIG. 1 as receiving an arm 105 another body part 102, such as a leg, may be inserted into an appropriately located and dimensioned body part aperture 30.

Still referring to FIG. 2a, the printing device 60 supports bi-directional printing of temporary tattoo art 101 by mounting a printing head 62a on a Y-axis guide rail 67 that guides the printing head 62a longitudinally and on parallel and arcuate first X-axis guide rail 68a and second X-axis guide rail 68b which rotationally move the printing head 62a. The ends of each X-axis guide rail 68a, 68b are affixed to the arm cylinder 31a using rail mounting brackets 70a (only two (2) of four (4) shown). The guide rails 67, 68a, 68b guide the printing head 62a as it moves above a large, rectangular print aperture 61 that is formed through the arm cylinder 31a. The printing head 62a then propels ink or another marker onto the print area 36 of the user's 100 arm 105 through the print aperture 61.

The printing head 62a is slidingly affixed to the Y-axis guide rail 67 via a sleeve-type first bearing 69a which allows smooth movement of the printing head 62a along the Y-axis guide rail 67. The ends of the Y-axis guide rail 67 are slidingly affixed to the arcuate first X-axis guide rail 68a and second X-axis guide rail 68b via respective second bearing 69b and third bearing 69c. The first bearing 69a includes an integral Y-axis motor 64 while the second and third bearings 69b, 69c includes integral X-axis motors 66. The motors 64, 66 drive their respective bearings 69a, 69b, 69c along respective guide rails 67, 68a, 68c to move the printing head 62a as required. The motors 64, 66 are envisioned as engaging the guide rails 67, 68a, 68b by utilizing a drive method such as, but not limited to: friction-type components, gear-tooth components, or other equivalent methods.

Printing and motor drive data is envisioned as being applied to the printing head 62a and motors 64, 66 via a multi-conductor ribbon cable 72 similar to as in conventional printers.

Figure 2B:
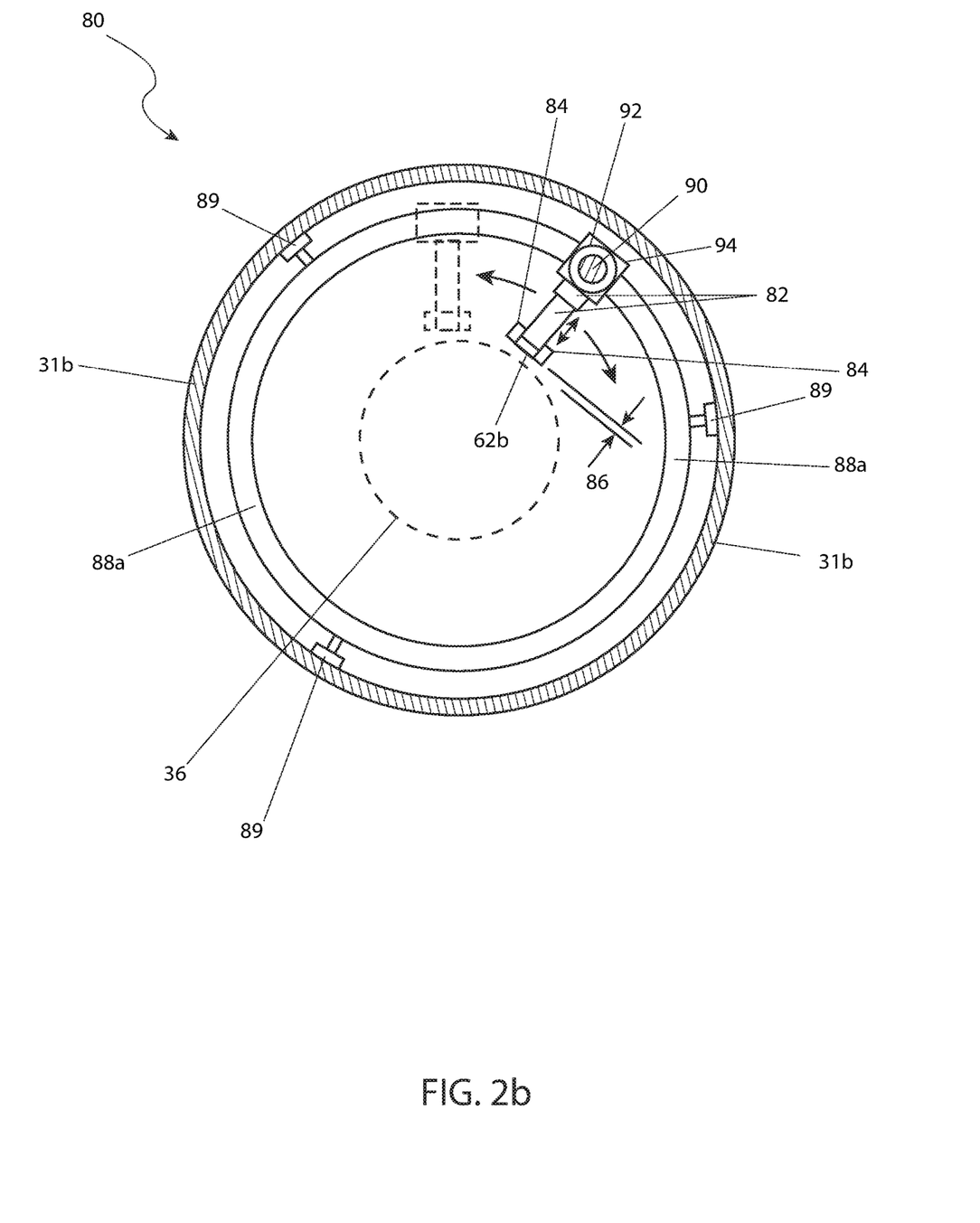
FIG. 2b is a sectional view of the printing device 80 shown in FIG. 2c taken along section line A-A of FIG. 2c.
Figure 2C:
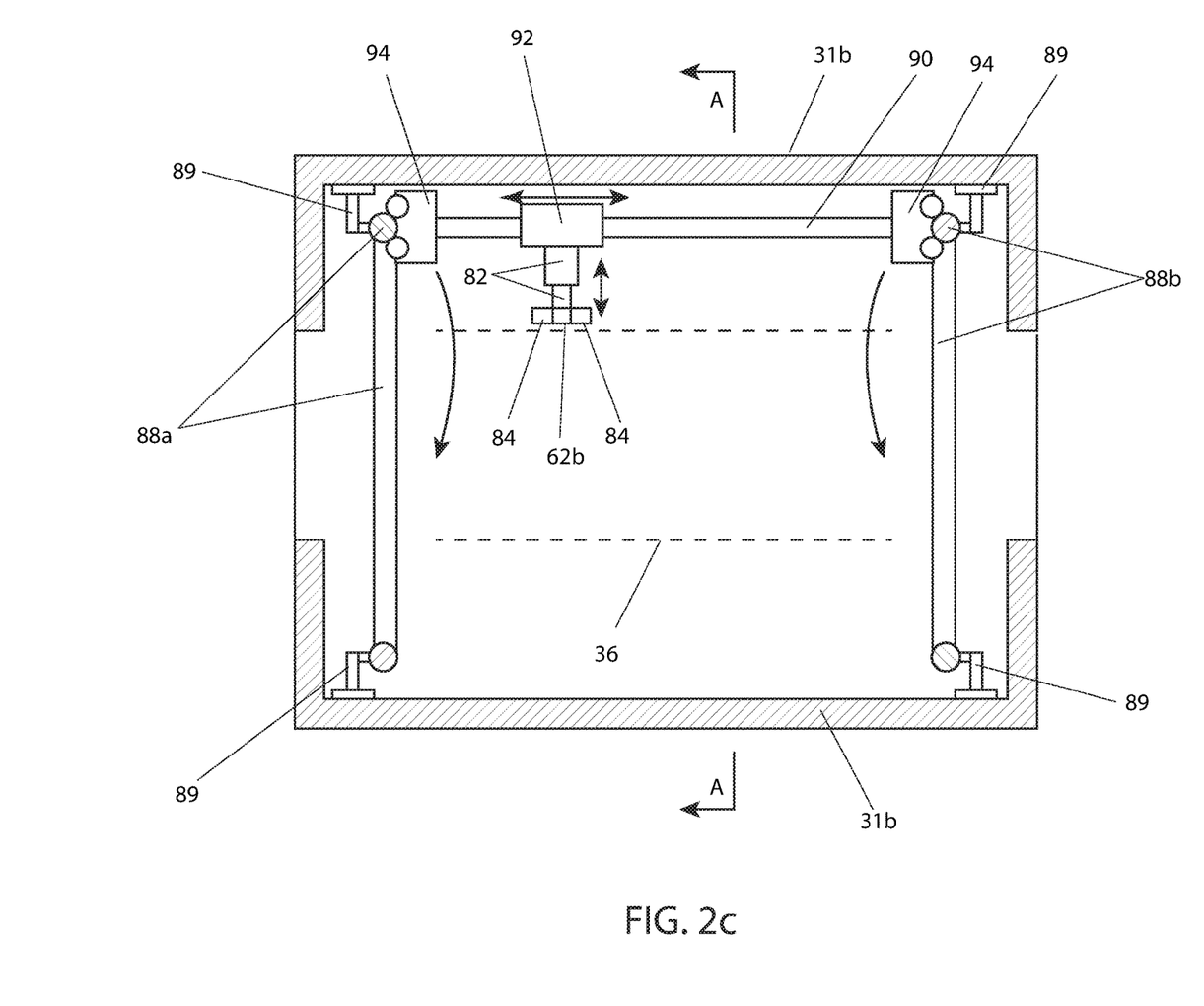
FIG. 2c is a side sectional view of a second printing device 80 suitable for use in temporary tattoo kiosks.

Referring now to FIGS. 2b and 2c for views of an alternative printing device 80 that is suitable for use in the seated temporary tattoo kiosk 10, as well as in other temporary tattoo kiosks that are described subsequently. The printing device 80 can apply temporary tattoo art 101 around a three-hundred sixty (360°) degree print area 36, such as a user's arm 105, leg, or torso. The second printing device 80 as a cylindrical arm cylinder 31b that contains parallel a first X-axis guide rail 88a and a second X-axis guide rail 88b, The X-axis guide rails 88a, 88b are affixed to the second arm cylinder 31b via X-axis guide rail brackets 89. The X-axis guide rails 88a, 88b are perpendicularly connected by a Y-axis guide rail 90 via respective first drive units 92 which enable the Y-axis guide rail 90 to the moved radially around the X-axis guide rails 88a, 88b. The Y-axis guide rail 90 includes a head positioning device 82 and a printing head 62b. The head positioning device 82 is affixed to the Y-axis guide rail 90 via a second drive unit 94. The head positioning device 82 provides a variable-length cylindrical member that is affixed to and is capable of accurately positioning the printing head 62b relative to a body part 102 in the arm cylinder 31b. In use, the guide rails 88a, 88b 90 move the head positioning device 82 and second printing head 62b longitudinally as well as laterally around a complete three-hundred sixty (360°) degree cylindrical print area 36.

Figure 3A:
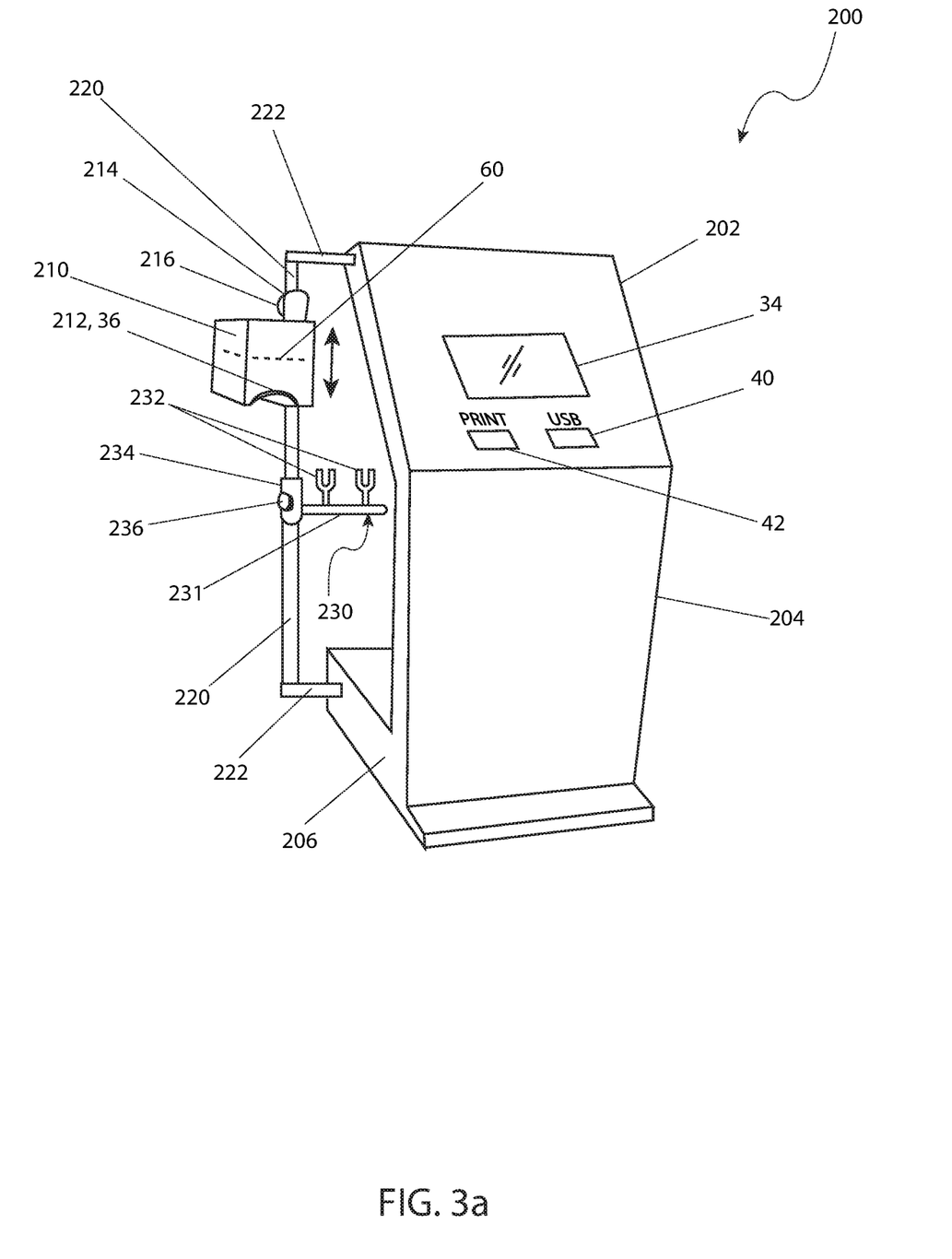
FIG. 3a is a front perspective view of a standing temporary tattoo kiosk 200 that is in accord with the present invention.
Figure 3B:
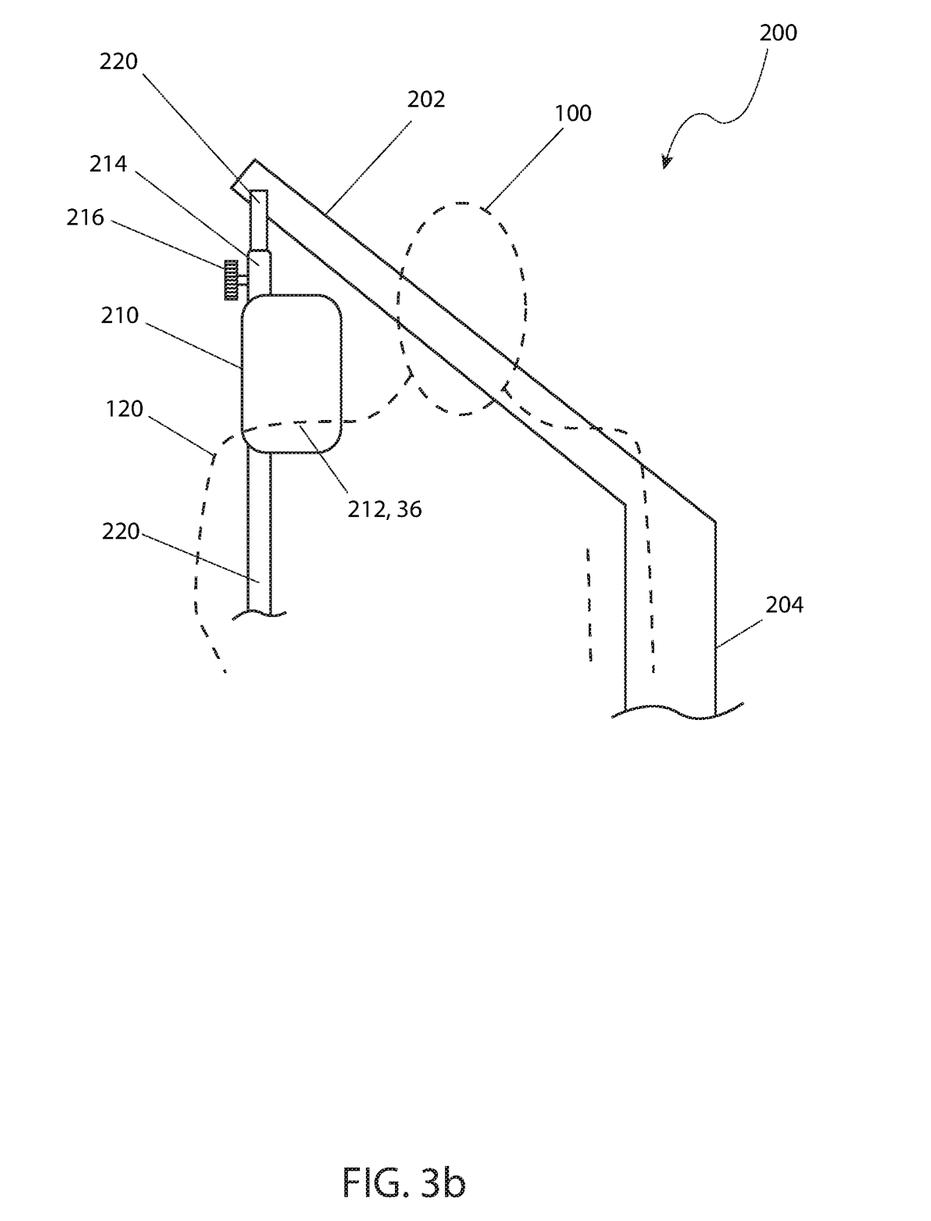
FIG. 3b is a partial cut-away side of the standing temporary tattoo kiosk 200 of FIG. 3a printing on a shoulder 120.

Refer now to FIGS. 3a and 3b for perspective and side views of a standing temporary tattoo kiosk 200 that is in accord with the present invention. The standing temporary tattoo kiosk 200 implements temporary tattoo art 101 imaging on body parts 102 of a user 100 while the user 100 is standing. The standing temporary tattoo kiosk 200 includes an upper cabinet section 202, a lower cabinet section 204, and a cabinet base 206.

The upper cabinet section 202 includes a digital display 34, a PRINT button 42, and a memory device slot 40. Along one (1) side of the standing temporary tattoo kiosk 200 is a vertically-adjustable printer housing 210 which contains a printing device 60 (see FIG. 2a). The bottom of the printer housing 210 is preferably a concave-shaped open area 212 that conforms to a body part 102 like a shoulder 120 onto which the temporary tattoo art 101 is to be applied. However, it should be understood that another embodiment of the printer housing 210 would provide a flat bottom surface for printing upon a flat body part 102 such as a user's 100 torso or back. The recessed area 212 defines a print area 36 within which the temporary tattoo art 101 is applied.

The printer housing 210 is supported by a vertical cylindrical post 220 which in turn is affixed to the upper cabinet section 202 and cabinet base 206 via respective connecting post mounting brackets 222. The height of the printer housing 210 from a subjacent floor surface can be adjusted based upon the height of a user 100 by sliding an integral printer positioning sleeve 214 of the printer housing 210 up or down upon the post 220. The position of the printer housing 210 is then secured by tightening a printer positioning sleeve knob 216 on the printer positioning sleeve 214.

In use, after selecting a desired temporary tattoo art 101 as previously described with regard to FIG. 1, the user 100 positions their shoulder 120 within the recessed area 212. The desired temporary tattoo art 101 is then applied through the recessed area 212 and onto the user's shoulder 120.

Figure 3C:
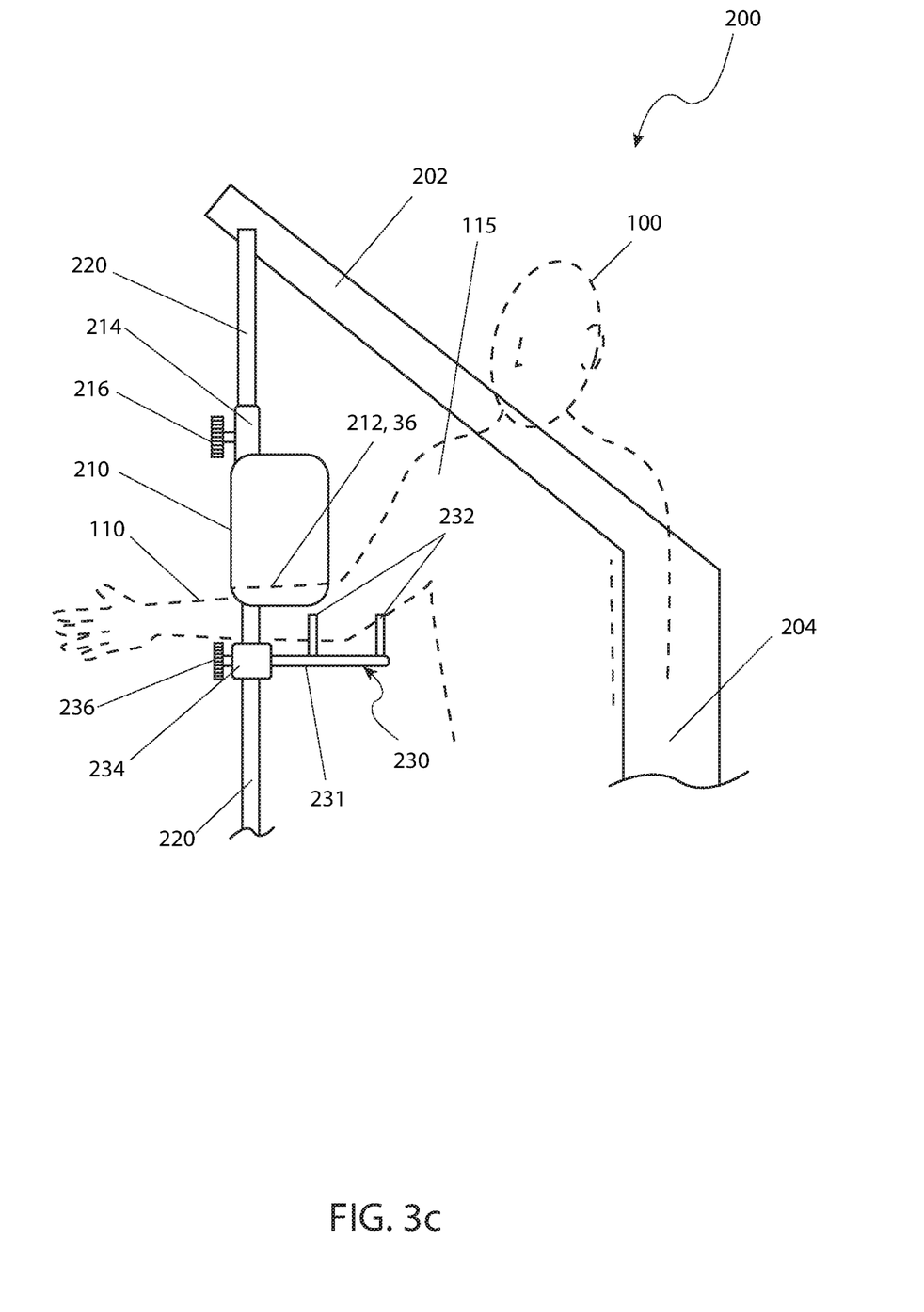
FIG. 3c is a partial cut-away side view of the standing temporary tattoo kiosk 200 of FIG. 3a printing on a forearm 110.

Referring now to FIG. 3c, the printer housing 210 can be lowered to a height level with a forearm 110 of the user 100 by using the printer positioning sleeve 214 and knob 216. The post 220 further includes a vertically adjustable arm restraint assembly 230 that is positioned adjacent to the printer positioning sleeve 214. The arm restraint assembly 230 acts as a forearm 110 stabilizer that is intended to improve printing quality. The arm restraint assembly 230 is adjustably affixed to the post 220 using an integral arm restraint positioning sleeve 234 and a corresponding arm restraint positioning sleeve knob 236. The arm restraint assembly 230 also includes a horizontal support rod 231 having a plurality of upwardly extending integral "U"-shaped arm saddles 232 that are sized and shaped to receive and support the forearm 110 of the user 100 (also reference FIG. 3a). When not in use, the arm restraint positioning sleeve knob 236 may be loosened and the arm restraint assembly 230 may be swung out of the way until needed.

It should be understood that the standing temporary tattoo kiosk 200 is not limited to the specifically illustrated embodiment of the arm restraint assembly 230. Many other variations could be developed or used with equal benefit, such as, but not limited to: pneumatic inflating devices, mechanical clamps, straps, and the like, and as such should not be interpreted as a limiting factor of the standing temporary tattoo kiosk 200.

Figure 4:
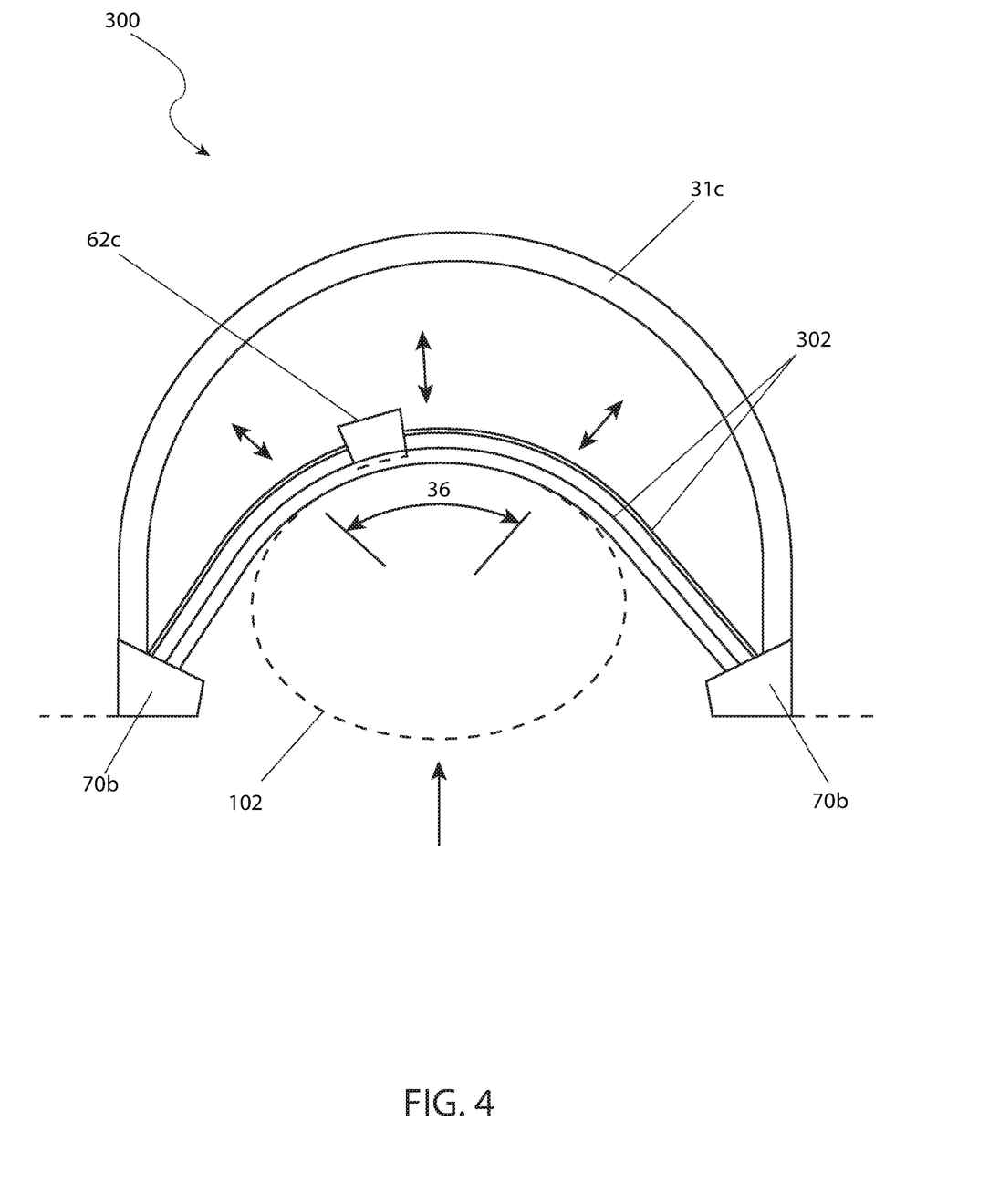
FIG. 4 is an end view of a printing device 300 having flexible guide rails 302.

Refer now to FIG. 4 for an end view of an alternate printing device 300 having flexible guide rails 302. The printing device 300 provides a similar bi-directional printing function to the one previously described with respect to the printing device 60. However, the printing device 300 includes flexible guide rails 302 which are positioned within an arm cylinder 31c. The arm cylinder 31c has a generally flat shape when at rest but readily forms an arcuate shape when displaced due to contact with a subjacent body part 102 such as an arm 105 or shoulder 120. The flexible guide rails 302 guide and position a printing head 62c in X-axis and Y-axis directions. The flexible guide rails 302 also act to maintain a constant distance between the third printing head 62c and the surface of the body part 102 to improve printing quality during application of the temporary tattoo art 101.

The printing device 300 is secured via a plurality of rail mounting brackets 70b to the arm cylinder 31c. It is envisioned that the intended print area 36 would cover an arcuate print area 36 of approximately forty-five degrees (45°). It is also envisioned that the printing device 300 good be utilized in lieu of the printing device 60 within the various embodiments such as the seated temporary tattoo kiosk 10 and the standing temporary tattoo kiosk 200.

Figure 5:
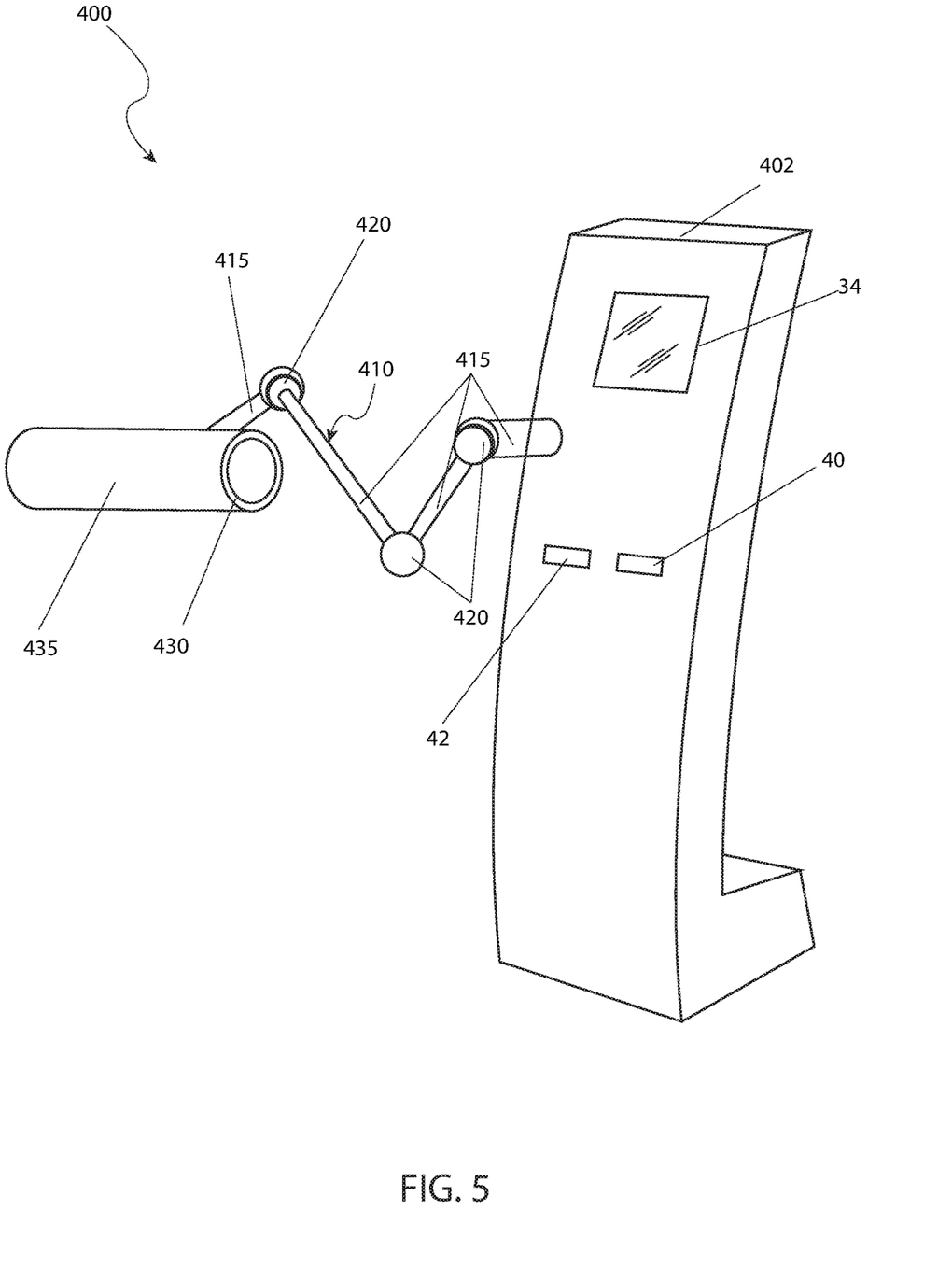
FIG. 5 is a perspective view of a positional printing arm tattoo kiosk 400; and, FIG. 6 is an operational block diagram 600 of the operation of the seated temporary tattoo kiosk 10 shown in FIG. 1 and which is suitable for use in the other described kiosks.

Referring now to FIG. 5, a perspective view of a positional printing arm tattoo kiosk 400 that enables variable positioning of a remote arm cylinder 435 that contains a printing device 60. The positional printing arm tattoo kiosk 400 provides increased access to a user's 100 various body parts 102 for printing temporary tattoo art 101.

The positional printing arm tattoo kiosk 400 includes an upright cabinet 402, a mechanically attached positionable mechanical arm 410, and a remote arm cylinder 435. The remote arm cylinder 435 provides both a protective enclosure for the printing device 60 and a cylindrical remote arm aperture 430 for access to the printing device 60. alternatively, the printing device 80 may be used. The remote arm aperture 430 and remote arm cylinder 435 provide similar printing functions as the previously described first arm cylinder 31a (see FIG. 2a).

The remote arm cylinder 435 may be positioned by a user 100 as needed via manual manipulation of the mechanical arm 410. The mechanical arm 410 supports three-dimensional positioning of the first printing device 60 via an assembly of linear arm elements 415 that are interconnected by orbitally manipulated friction-type arm joints 420. Such enables positioning the remote arm cylinder 435 vertically, horizontally, diagonally, and the like. The opposing ends of the mechanical arm 410 are respectively affixed to the cabinet 402 and to the remote arm cylinder 435. The cabinet 402 provides similar features and functions as the previously described standing temporary tattoo kiosk 200, including features such as, but not limited to: a video display 34, a memory device slot 40, and a PRINT button 42.

Figure 6:
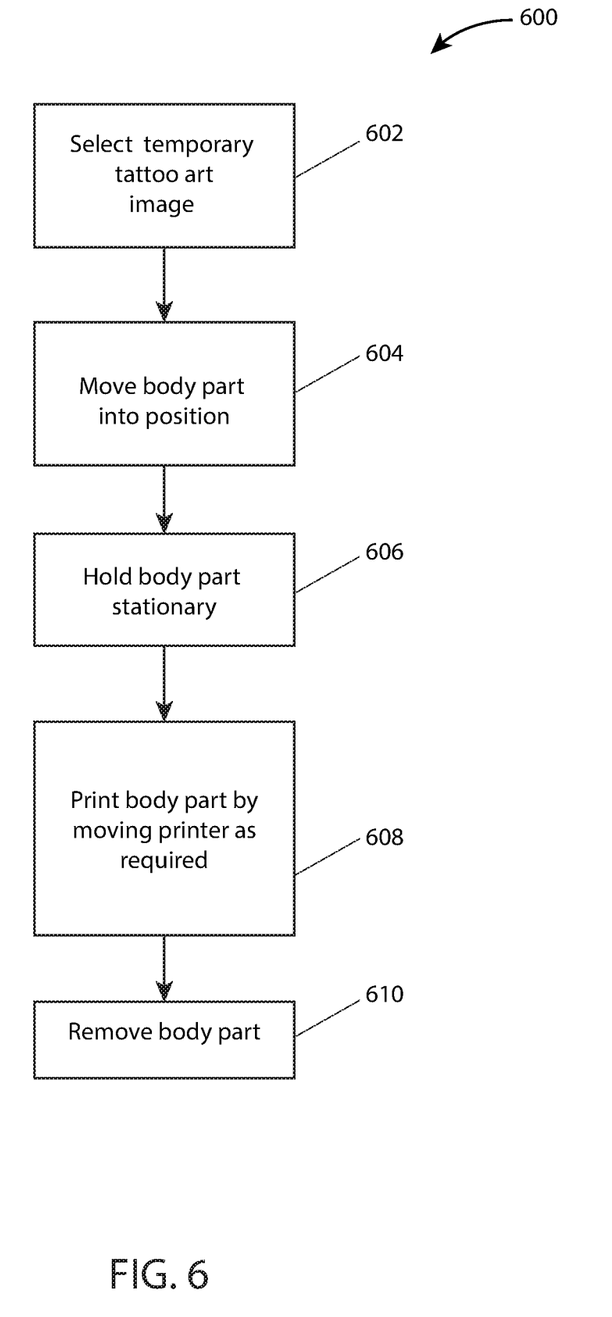

Refer now to FIG. 6 for an operational block diagram 600 of the various embodiments of the temporary tattoo kiosks. At step 602 the user 100 selects a temporary tattoo art 101 image for the user's body part 102. At step 604 the user 100 moves the body part 102 into position in anticipation of printing the body part 102. Next, at step 606 the user 100 holds the body part 102 stationary for the printing process. At step 608 printing occurs as the printing device 60 is moved as required to have the printing head 62a print the temporary tattoo art 101 on the body part 102. At step 610 the body part 102 is removed from the seated temporary tattoo kiosk 10.

The various embodiments of the present invention can be utilized by the common user in a simple and effortless manner with little or no training. For example, the method of installing and utilizing the seated temporary tattoo kiosk 10 may be achieved by performing the following steps: procuring a model of the seated temporary tattoo kiosk 10 having a body part aperture 30 and a printing device 60 (or printing device 80) configured to enable printing a temporary tattoo art 101 image onto a desired body part 102; placing the seated temporary tattoo kiosk 10 at a desired location such as, but not limited to: a tattoo parlor, a shopping center, a hotel, or the like; allowing a user 100 to be seated upon the seat 125; allowing the user 100 or another person to utilize the video display 34 and/or the memory device slot 40 to select a desired temporary tattoo art 101 image and to input various settings to control the seated temporary tattoo kiosk 10; downloading the selected temporary tattoo art 101 image from an internal library, an internet connection, a Bluetooth® device, or a personal memory storage device via engagement with the memory device slot 40; inserting the user's arm 105 into the body part aperture 30; positioning the user's 100 body part 102 relative to the print aperture 61; pressing the PRINT button 42 to initiate printing of the temporary tattoo art 101; holding the body part 102 stationary during printing; allowing the printing of the temporary tattoo art 101 to occur; observing the printing of the temporary tattoo art 101 through the viewing window 38, if desired; removing the body part 102 from the body part aperture 30; and, benefiting from a customized temporary tattoo art 101 image afforded a user of the seated temporary tattoo kiosk 10.

The method of installing and utilizing the standing temporary tattoo kiosk 200 is envisioned to be similar to that of the seated temporary tattoo kiosk 10, but with the following changes: procuring a desired model of the standing temporary tattoo kiosk 200; utilizing the digital display 34 to select or download a temporary tattoo art 101 image to be printed; inputting desired settings; using the printer positioning sleeve 214 and printer positioning sleeve knob 216 to adjust the printer housing 210 to a desired height based upon the height of a user 100 and the intended body part 102 to receive the temporary tattoo art 101 image; positioning the height and position of the arm restraint assembly 230, as needed, to support and stabilize the body part 102, such as an arm 105, by positioning the arm saddle 232 of the arm restraint assembly 230 under the arm 105; using the arm restraint positioning sleeve 234 and arm restraint positioning sleeve knob 236 to secure the arm restraint assembly 230 in position; pressing the PRINT button 42 to initiate printing of the selected temporary tattoo art 101 image onto the positioned body part 102; allowing the printing of the temporary tattoo art 101 image to occur; lowering and swinging the arm restraint assembly 230 out of the way; and, removing the body part 102 from the standing temporary tattoo kiosk 200.

The method of utilizing the positional printing arm tattoo kiosk 400 is envisioned to being similar to that of the seated temporary tattoo kiosk 10, but with the following changes: procuring a model of the positional printing arm tattoo kiosk 400 being configured for one (1) or more desired body parts 102; utilizing the digital display 34 and/or memory device slot 40 to select or download a temporary tattoo art 101 to be printed; utilizing the digital display 34 to input desired settings; positioning the remote arm cylinder 435 by manually manipulating the mechanical arm 410 until obtaining a desired position relative to the body part 102; inserting the body part 102 into the remote arm cylinder 435; pressing the PRINT button 42 to initiate printing of the selected temporary tattoo art 101 onto the positioned body part 102; holding the body part 102 stationary during the printing process; allowing the printing of the temporary tattoo art 101 to occur; removing the body part 102 from the remote arm cylinder 435; and, replacing the remote arm cylinder 435 and mechanical arm 410 to their home position for subsequent usage.

The method of utilizing the printing device 300 may be achieved by performing the following steps: motioning a body part 102 so as to apply pressure against the flexible guide rails 302 of the third printing device 300; continuing to press the body part 102 against the flexible guide rails 302 until the flexible guide rails 302 take on an arcuate form of approximately forty-five degrees (45°) relative to the body part 102; pressing the PRINT button 42 to initiate printing of the selected temporary tattoo art 101; allowing time for the printing of the temporary tattoo art 101; and, removing the body part 102 from the kiosk 10, 200, 300.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. A positional printing arm tattoo kiosk, comprising:
    an upright cabinet having a cylindrical remote arm aperture disposed on said upright cabinet for access to a tattoo printing device inside said upright cabinet;
    a positionable mechanical arm providing three-dimensional positioning of the tattoo printing device via an assembly of linear arm elements that are interconnected by a plurality of orbitally manipulated friction-type arm joints;
    a remote arm cylinder providing a protective enclosure for the printing device, said remote arm cylinder is manually positioned by said mechanical arm;
    wherein said positional printing arm tattoo kiosk provides increased access to said user's body parts for printing temporary tattoo art onto said user's body parts;
    wherein said orbitally manipulated friction-type arm joints enable positioning of said remote arm cylinder; and
    wherein a first end of said mechanical arm is respectively affixed to said upright cabinet and a second end of the mechanical arm is respectively affixed to said remote arm cylinder.

2. The positional printing arm tattoo kiosk according to claim 1,
    wherein said upright cabinet includes a video display, a memory device slot, and a PRINT button.

* * * * *